United States Patent [19]

Shih et al.

[11] 4,176,131

[45] Nov. 27, 1979

[54] CHEMICAL PROCESS

[75] Inventors: Kun M. Shih, East Syracuse; Derek Walker, Jamesville, both of N.Y.

[73] Assignee: Bristol-Myers Company, New York, N.Y.

[21] Appl. No.: 966,177

[22] Filed: Dec. 4, 1978

[51] Int. Cl.² .......................... C07F 7/10; C07F 7/18
[52] U.S. Cl. ...................... 260/448.2 E; 260/448.8 R
[58] Field of Search .................. 260/448.2 E, 448.8 R

[56] References Cited

U.S. PATENT DOCUMENTS

| | | | |
|---|---|---|---|
| 2,532,559 | 12/1950 | Klein | 260/448.2 E X |
| 3,466,314 | 9/1969 | Moedritzer et al. | 260/448.2 E X |
| 3,642,854 | 2/1972 | Kozjukov et al. | 260/448.2 E |
| 3,987,061 | 10/1976 | Pedersen | 260/448.8 R X |

FOREIGN PATENT DOCUMENTS

| | | | |
|---|---|---|---|
| 1205099 | 11/1965 | Fed. Rep. of Germany | 260/448.2 E UX |
| 1965741 | 7/1971 | Fed. Rep. of Germany | 260/448.2 E UX |
| 643941 | 9/1950 | United Kingdom | 260/448.8 R UX |
| 1373291 | 11/1974 | United Kingdom | 260/448.2 E UX |

OTHER PUBLICATIONS

JACS, 70, pp. 1043 and 1222, 1948.
JACS, 72, p. 196, 1950.
J. Org. Chem., 28, p. 586, 1963.
J.A.C.S., 72, p. 3045, 1950.
"Chem. Ber.", 93, p. 1111, 1960.
"Synthesis", 1976, pp. 168-184, 1976.
"Angewandte Chemie", International Ed., 16, p. 493, 1977.

*Primary Examiner*—Paul F. Shaver
*Attorney, Agent, or Firm*—Richard R. Lloyd

[57] ABSTRACT

Optionally substituted silicon isocyanates are prepared by reacting a corresponding silicon halide with an alkali metal cyanate or an alkaline earth metal cyanate in an inert solvent having a dielectric constant below about 10, in the presence of a crown ether as a catalyst.

10 Claims, No Drawings

CHEMICAL PROCESS

SUMMARY OF THE INVENTION

This application relates to an improved process for the preparation of optionally substituted silicon isocyanates which comprises reacting a corresponding silicon halide with an alkali metal cyanate or an alkaline earth metal cyanate in an inert solvent having a dielectric constant below about 10, in the presence of a crown ether as a catalyst.

BACKGROUND AND PRIOR ART

Silicon tetraisocyanate and various organosilyl isocyanates have classically been prepared by heating a silicon tetrahalide or an organosilyl halide with silver isocyanate in an inert organic solvent such as benzene. See, for example, *J. Am. Chem. Soc.*, 70, 1042 (1948), *J. Am. Chem. Soc.*, 70, 1222 (1948) and *J. Am. Chem. Soc.*, 72 196 (1950), and references cited therein.

*J. Org. Chem.*, 28, 586 (1963) discloses, inter alia, the preparation of silicon tetraisocyanate, trimethylsilyl isocyanate and dimethylsilyl diisocyanate by reacting the appropriate silyl halide with isocyanic acid (prepared by cracking isocyanuric acid at about 600° C.) in an inert solvent, using trimethylamine or pyridine as a proton acceptor.

U. K. Patent No. 643,941 discloses, inter alia, the preparation of methylsilyl isocyanates by heating the appropriate methylsilyl halide with an alkali metal cyanate in a pressure vessel at a temperature of about 300°-335° C.

*J. Am. Chem. Soc.*, 72, 3045 (1950) describes the preparation of triphenylsilyl isocyanate by (A( fusing triphenylsilyl chloride with urea and (B) heating triphenylsilyl chloride with silver cyanate or sodium urethan in an inert organic solvent.

*Chem. Ber.*, 93, 1111 (1960) discloses the preparation methylsilyl isocyanates by the reaction of the appropriate methylsilyl halide (A) with lead cyanate in an inert solvent, (B) with potassium cyanate in an inert solvent with concentrated sulfuric acid or acetic acid as catalyst and (C) with urea at a temperature of from 280° C. to 340° C. and at pressures of from 45 to 105 atmospheres.

West German DAS No. 1,205,099 discloses the preparation of organosilyl isocyanates of the formula

wherein R is (lower)alkyl, (lower)alkoxy or phenoxy and n is 2-3 by the reaction of an organosilyl halide of the formula

in which X is halogen, with an alkali metal cyanate in liquid sulfur dioxide at a temperature of about −25° C. to 70° C. Above the boiling point of sulfur dioxide (−10° C.) the reaction must be conducted in a pressure vessel.

U. K. Pat. No. 1,373,291 discloses the preparation of organic isocyanates (such as benzyl isocyanate and xylylene diisocyanate) by the reaction of the appropriate organic halide (in which the halogen must be aliphatically bound) with an alkali metal cyanate, an alkaline earth metal cyanate or an ammonium cyanate in the presence of a crown ether. The reaction may be conducted in the absence of solvent or in an inert polar or non-polar organic solvent, or a mixture thereof.

West German OLS No. 1,965,741 discloses, inter alia, the preparation of organosilyl isocyanates of the formula

wherein R is alkoxy, aryloxy, alkenyl, SiO-, or substituted or unsubstituted alkyl, aralkyl or aryl, and n is 0-3, by reacting an organosilyl halide of the formula

wherein R and n are as above and X is halogen, with an alkali metal cyanate or an ammonium cyanate in the presence, as catalyst, of a polar organic solvent having a dielectric constant of at least 10, e.g. dimethylformamide, dimethylacetamide, N-methylpyrrolidone cyclohexanone or benzonitrile. The polar solvent may be used in admixture with an inert non-polar organic solvent.

It will be appreciated that, although numerous procedures for the preparation of silyl isocyanates have been described, most of these involve the use of expensive chemicals (such as silver cyanate), high cost or otherwise generally undesirable technology (such as high temperature, high pressure, use of liquid sulfur dioxide, or the like) or low yield.

It is known that certain two-phase reactions between active halides (generally organic halides) and nucleophiles are catalyzed by quaternary ammonium salts, quaternary phosphonium salts and by crown ethers; such reactions are referred to as examples of phase transfer catalysis. The field of phase transfer catalysis is fairly new and not fully understood. Thus, no general rules have been formulated which allow one to identify reactions which will proceed by phase transfer catalysis. Many factors such as substrate structure, nucleophile, solvent, phase transfer catalyst structure and reaction conditions all appear to play a part in unpredictable ways. Furthermore, the successful applications of phase transfer catalysis are largely in the field of organic chemistry. These appear to be no examples in which alkali metal cyanates have been successfully reated with silyl halides under phase transfer catalysis conditions to give silyl isocyanates. Indeed, early attempts by us to use quaternary ammonium type phase transfer catalysts to prepare silyl isocyanates failed. Thus, when trimethylchlorosilane and sodium or potassium cyanate were stirred in toluene in the presence of tetrabutylammonium iodide, no trimethylsilyl isocyanate could be detected in the reaction mixture. To our surprise, however, when a small amount of 18-crown-6 ether was added to the reaction mixture a very vigorous reaction took place leading to a virtually quantitative yield of trimethylsilyl isocyanate.

A review of phase transfer catalysis, including the use of crown ethers as phase transfer catalysts, is found in *Angewandte Chemie*, International Edition, 16, 493 (1977). A review of the principles and applications of crown ether chemistry is found in *Synthesis*, 1976, 168-184.

Complete Disclosure

This invention relates to a process for the preparation of silyl isocyanates of the formula

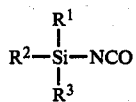

wherein $R^1$, $R^2$ and $R^3$ each are independently hydrogen, isocyanato, (lower)alkyl, (lower)alkoxy, phenyl, phenoxy, phenyl (lower)alkyl, phenyl(lower)alkoxy or cycloalkyl; which process comprises reacting a halogen compound of the formula

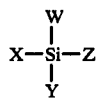

wherein W is $R^1$, chloro, bromo, fluoro or iodo; X is $R^2$, chloro, bromo, fluoro or iodo; Y is $R^3$, chloro bromo, fluoro or iodo; and Z is chloro, bromo, fluoro or iodo; with an alkali metal cyanate, in an inert solvent having a dielectric constant below about 10, at a temperature of from about 0° C. to about 200° C., in the presence of a crown ether as a catalyst.

In a preferred embodiment, this invention relates to a process for the preparation of silyl isocyanates of the formula

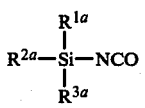

wherein $R^{1a}$, $R^{2a}$ and $R^{3a}$ each are independently hydrogen, isocyanato, (lower)alkyl, (lower)alkoxy, phenyl or phenoxy; which process comprises reacting a halogen compound of the formula

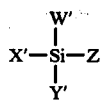

wherein W' is $R^{1a}$, chloro, bromo, fluoro or iodo (and most preferably $R^{1a}$, chloro, bromo or fluoro); X' is $R^{2a}$, chloro, bromo fluoro or iodo (and most preferably $R^{2a}$, chloro, bromo or fluoro); Y' is $R^{3a}$, chloro, bromo, fluoro or iodo (and most preferably $R^{3a}$, chloro, bromo or fluoro); and Z is chloro, bromo, fluoro or iodo (and most preferably chloro, bromo or fluoro); with sodium cyanate or potassium cyanate (and most preferably with sodium cyanate) in an inert solvent having a dielectric constant below about 10, at a temperature of from about 25° C. to about 150° C. (and most preferably from about 50° C. to about 100° C.), in the presence of a crown ether as a catalyst.

In a more preferred embodiment of the invention the crown ether catalyst is 18-crown-6 ether, dibenzo-18-crown-6 ether, 1,10-diaza-18-crown-6 ether, dicyclohexo-18-crown-6 ether, 2,6-diketo-18-crown-6 ether, 1,10-dithia-18-crown-6 ether, 15-crown-5 ehter, benzo-15-crown-5 ether, 4-tert-butylbenzo-15-crown-5 ether, 4-tert-butylcyclohexo-15-crown-5 ether, cyclohexo-15-crown-5 ether, 1,4,7-trithia-15-crown-5 ether, 21-crown-7 ether or 12-crown-4 ether. In a still more preferred embodiment of the invention the crown ether catalyst is 18-crown-6 ehter, dibenzo-18-crown-6 ether, 15-crown-5 ether or 12-crown-4 ether. The most preferred catalysts are 18-crown-6 ether and 15-crown-5 ether.

In preparing a silyl isocyanate of Formula I, the silyl halide of Formula II is theoretically reacted with one equivalent of alkali metal cyanate for each isocyanate group which is to be introduced; however, more or less than one equivalent may be utilized. Generally, when complete conversion of the halogen leaving groups on the compound of Formula II is desired, one utilizes from 1 equivalent to an excess of about 1.5 equivalents of alkali metal cyanate for each halogen. Thus, one would normally utilize from about 1 to 1.5 equivalents of alkali metal cyanate to convert a monohalosilane to a silyl monoisocyanate, from about 2 to 3 equivalents of alkali metal cyanate to convert a dihalosilane to a silyl diisocyanate, from about 3 to 4.5 equivalents of alkali metal cyanate to convert a trihalosilane to a silyl triisocyanate, and from about 4 to 6 equivalents to convert a silicon tetrahalide to silicon tetraisocyanate. The use of less than an equivalent of alkali metal cyanate for each halogen in the starting compound of Formula II will result in the production of mixtures containing chlorosilyl isocyanates. The use of more than 1.5 equivalents of alkali metal cyanate for each halogen in the starting compound of Formula II is generally not detrimental to the reaction, but no benefit is usually obtained by such an excess. We normally prefer to utilize from about the theoretical amount of alkali metal cyanate up to about 5–10% excess.

The amount of crown ether catalyst which is utilized may vary over a wide range. In some cases (depending on particular reactants, solvent, crown ether and temperature), the crown ether may be useful in only parts per million quantities, but it is usually utilized in the range of from about 0.1% to about 10% of the weight of the starting compound of Formula II. More than 10% may be utilized but no benefit is usually obtained thereby. We normally prefer to utilize an amount of crown ether catalyst which is equal to from about 1% to about 2% of the weight of the compound of Formula II.

Suitable inert solvents having a dielectric constant (D.C.) below about 10 will be apparent to those skilled in the art. They include, for example, methylene chloride (D.C.=9.08), 1,2-dichloroethane (D.C.=10.45), trichloroethylene (D.C.=3.4), n-heptane (D.C.=1.9), ethyl acetate D.C.=6.02), methyl benzoate (D.C.=6.59), benzene (D.C.=2.28), toluene (D.C.=2.38), m-xylene (D.C.=2.38), mineral oil (D.C.=2.13), silicone oil (D.C.=2.58), Therminol 55 (D.C.=2-3), Dowtherm A (D.C.=3.35), biphenyl (D.C.=2.53) and diphenyl ether (D.C.=3.65).

Although the reaction may be carried out in relatively low boiling solvents, it is often preferred to utilize high boiling solvents in order to simplify separation of the product from the reaction mixture. If the product and the solvent have similar boiling points one must utilize careful fractional distillation to obtain pure product. If the solvent boils at a lower temperature than the product, one must distill off the solvent before distilling or otherwise recovering the desired product. In the preparation of typical products such as trimethylsilyl isocyanate (b.p. 91° C.), dimethylsilyl diisocyanate (b.p. 139°–140° C.), methylsilyl triisocyanate (b.p. 171° C.) and silicon tetraisocyanate (b.p. 186° C.), we find it particularly convenient to conduct the reaction in a high-boiling solvent such as Dowtherm A (b.p. ca. 257°

C.). In this solvent, high yields of pure product may be obtained by simple distillation of the product from the Dowtherm A/crown ether and, in addition, the Dowtherm A/crown ether solution may be reused. Periodically, the by-product salt (e.g. NaCl) may be filtered from the Dowtherm A/crown ether solution or washed out with water, in order to extend the usage of the Dowtherm A/crown ether solution. When it is desired that the unwanted salts are washed out with water, the crown ether preferably is one which is soluble in the organic medium and relatively insoluble in water or aqueous salt solution.

The silyl isocyanates produced by the process of this invention are known compounds with known utilities. See, for example, U.K. Patent No. 643,941 which discloses the use of methylsilyl isocyanates in rendering materials water repellant. A particularly valuable utility of the silyl isocyanates of Formula I is disclosed in our colleagues U.S. Patent Application Ser. No. 893,092, filed Apr. 3, 1978, the entire disclosure of which is incorporated herein by reference. As disclosed therein, penicillin sulfoxide esters are reacted with an isocyanate (including silyl isocyanates of Formula I herein) to produce the corresponding (substituted)-2-carbamoyloxymethylpenam, the corresponding (substituted)-3-carbamoyloxycepham or the corresponding 3-methylcephem. The following Illustrative Procedure describes the use of dimethylsilyl diisocyanate for the ring expansion of the diphenylmethyl ester of penicillin V sulfoxide to produce the corresponding 3-methylcephem compound.

ILLUSTRATIVE PROCEDURE

Preparation of (6R,7R) 3-Methyl-7-phenoxyacetamidoceph-3-em-4-carboxylic Acid Diphenylmethyl Ester (1S,3S,5R,6R) 2,2-Dimethyl-6-phenoxyacetamidopenam-3-carboxylic acid-1-oxide diphenylmethyl ester (25.00 gms, 45.41 mmoles) was dissolved in sieve-dried, peroxide-free dioxane (250 mls) at 25° C. with good agitation. To this solution, in order, were added pyridine (10.99 mls, 10.78 gms, 136.22 mmoles), acetyl bromide (0.67 mls, 1.12 gms, 9.08 mmoles) and dimethylsilyl diisocyanate (16.14 gms, 113.51 mmoles), and the slurry was heated to reflux (ca. 100° C.) for 4 hours. The dioxane slurry was then cooled to 25° C., filtered, and concentrated in vacuo at 50° C. to a heavy oil. The oil was taken up in methylene chloride (400 mls), stirred for 15 minutes at 25° C., filtered, and concentrated in vacuo to dryness. The residue was dissolved in hot 1-butanol (500 mls, ca. 90°–95° C.) and allowed to cool to 25° C. The slurry was cooled to 0°–5° C. for 16 hours, filtered, washed with cold butanol (0°–5° C., 100 mls), then with Skellysolve B (200 mls), and oven-dried at 45° C. to constant weight. Yield: 20.2 gms, 86.4% of snow-white crystalline title compound. The NMR spectrum was clean and consistent for the desired structure, as follows:

80 MHz H' NMR, $\delta(CD_2Cl_2)$ 2.08 (3H, s, $CH_3$), 3.04–3.62 (2H, m, $CH_2$, $J_{AB}=18.1$ Hz), 4.55 (2H, s, $CH_2$), 4.99–5.05 (1H, d, $\beta$-lactam H, $J_A=4.7$ Hz), 5.74–5.91 (1H, m, $\beta$-lactam H, $J=4.7$ Hz), 6.75–7.50 (17H, m, aromatic CH, and NH).

Dowtherm A is a registered trademark of Dow Chemical Company for a heat transfer medium consisting of a eutectic mixture of biphenyl and diphenyl ether.

Therminol 55 is a registered trademark of the Monsanto Company for a heat transfer medium consisting of a mixture of alkylated aromatics having an average molecular weight of 340, a typical specific gravity of 0.895 and a typical refractive index $n_{25}^D$ 1.5035.

Skellysolve B is a registered trademark of the Skelly Oil Company for a petroleum ether fraction consisting essentially of n-hexane.

As used herein and in the claims, the term "(lower)alkyl" means a straight or branched chain alkyl group containing from 1 to 6 carbon atoms. Similarly, the term "(lower)alkoxy" means an alkoxy group in which the alkyl moiety is as defined above.

The silyl halides of Formula II used as starting materials are either known materials (many of which are commercially available) or may be prepared by well-known procedures.

The crown ethers used as catalysts are known compounds and most are commercially available.

EXAMPLE 1

Preparation of Trimethylsilyl Isocyanate in m-Xylene

A suspension of sodium cyanate (6.5 g, 0.1 mole) in m-xylene (20 ml) containing 18-crown-6 ether (0.1 g, 0.378 m mole) as catalyst was treated dropwise with trimethylchlorosilane (10.96 g, 0.1 mole) over a period of 20 minutes with vigorous agitation. The reaction commenced spontaneously with a remarkable heat of reaction. The resultant slurry was stirred at 55°–57° C. for 30 minutes and then at 90° C. for 4 hours. The progress of the reaction was followed by the disappearance of the $\underline{CH_3}SiCl$ signal at 0.42 ppm in the proton nmr and the appearance of the $\underline{CH_3}SiNCO$ signal at 0.25 ppm. The trimethylsilyl isocyanate was distilled directly from the higher-boiling m-xylene (bp 91°, 760 mm). The colorless crude liquid trimethylsilyl isocyanate was obtained in 100% yield (11.5 g) with a purity of 90–95%. A strong infrared band was present at 2285 $cm^{-1}$, characteristic of isocyanates. CFT-20 H'mr and mass spectra showed a small amount of xylene as contaminant, m/e=115 ($Me_3SiNCO$), 100 ($(CH_3)_2SiNCO$, 76 (SiNCO), 42 (NCO), 28 (CO).

EXAMPLE 2

Preparation of Dimethylsilyl Diisocyanate in Dowtherm A (A) Sodium cyanate (65 g, 1.0 mole) was suspended in 200 ml Dowtherm A in the presence of 18-crown-6 ether (1.5 g, 5.68 m mole) and the slurry was cooled in a 25° C. water bath. To this slurry was added dimethyldichlorosilane (64.5 g, 0.5 mole) over a period of 28 minutes and the mixture was stirred at 60° C. for one hour. The agitated mixture was then heated at 90°–93° C. for 3 hours. The product was distilled directly from the higher-boiling Dowtherm A. Dimethylsilyl diisocyanate boiling at 132° C., under slight reduced pressure, was distilled in 92.3% yield. CFT-20 H'mr shown a trace of Dowtherm A contamination. The purity was 98–99%. The infrared spectrum of dimethylsilyl diisocyanate showed two isocyanate absorptions at 2280 $cm^{-1}$ and 2300 $cm^{-1}$.

(B) The Dowtherm/18-crown-6/sodium chloride slurry was filtered and the Dowtherm A solution reused without adding fresh 18-crown-6 ether. Thus, addition of fresh sodium cyanate (65 g, 1.0 mole) and fresh dimethyldichlorosilane (64.5 g, 0.5 mole) and reaction as above gave 98–99% pure dimethylsilyl diisocyanate in 92% yield.

EXAMPLE 3

Preparation of Dimethylsilyl Diisocyanate in Toluene

Dimethyldichlorosilane (12.9 g, 0.1 mole) was reacted with sodium cyanate (13.2 g, 0.2 mole) in dry toluene (40 ml) in the presence of 18-crown-6 ether (0.2 g) according to the procedure of Example 2A. The suspension was then quickly filtered through a sintered glass funnel inside a nitrogen bag to remove the sodium chloride, and the toluene was removed from the product by distilling at 110° C./760 mm Hg. The residual oil was then distilled at 100° C./250 mm Hg to give a yield of 84.5%.

IR: 2280 cm$^{-1}$, 2320 cm$^{-1}$ (NCO).

NMR: Showed heavy toluene contamination. The purity was 60–70%.

EXAMPLE 4

Preparation of Methylsilyl Triisocyanate in Toluene (A) Sodium cyanate (97.5 g, 1.5 mole) was suspended in 200 ml of dry toluene and 18-crown-6 ether (1.5 g) was added. Methyltrichlorosilane (74.8 g, 0.5 mole) was slowly added over 1 hour. A striking exothermic heat was noticed. The slurry was agitated at 60° C. for 1 hour and then at 90°–100° C. for 4 hours. The reaction mixture was then filtered inside a nitrogen bag and the solid was washed with 100 ml of fresh toluene. After removing the toluene by fractional distillation, 58.6 g (69.4%) of colorless methylsilyl triisocyanate was collected at bp 163° C./760 mm Hg.

IR: 2280 cm$^{-1}$ (NCO)

NMR: Showed 5–10% toluene contamination.

Further material was found to be present in the distillation forecuts.

(B) The above reaction was repeated using 0.1 mole methyltrichlorosilane and 0.3 mole of sodium cyanate. There was obtained an 85.8% yield (purity was 79.2%) with 0.5 mole equivalent of toluene in the product.

EXAMPLE 5

Preparation of Methylsilyl Triisocyanate in Dowtherm A

Sodium cyanate (195 g, 3.0 mole) was suspended in 300 ml of Dowtherm A and 18-crown-6 ether (3 g) was added. Methyltrichlorosilane (149 g, 1 mole) was slowly added to the suspension over a period of 1 hour, with water cooling. The slurry was heated and stirred at 60°–63° C. for 20 minutes and then at 100° C. for 4 hours. The product was then distilled directly from the reaction mixture. A yield of 75.1% (123.5 g) was recovered at bp 161° C./500–540 mm Hg. Forecuts contained additional material.

NMR: Showed 7.35% Dowtherm A contamination.

EXAMPLE 6

Preparation of Silicon Tetraisocyanate in Toluene

Sodium cyanate (34 g, 0.52 mole) and 18-crown-6 ether (0.3 g) were suspended in 40 ml of dry toluene. Silicon tetrachloride (16.99 g, 0.1 mole) was slowly added to the vigorously agitated suspension over 30 minutes. Water cooling was necessary. The slurry was then heated and stirred between 60°–70° C. for 1.5 hours. The sodium chloride was removed from the reaction mixture by filtration inside a nitrogen bag and the cake was washed with 20 ml of dry heptane. The heptane and toluene were removed by distillation at 90°–100° C./760 mm Hg. The yield was 63.6% (12.49 g). There were no chloride intermediates or solvents in its mass spectra.

IR: 2280 cm$^{-1}$ (NCO)

Mass Spectra: m/e=28 (CO), 42 (NCO), 70 (SiNCO), 112 (SiNCO)$_2$, 154 Si(NCO)$_3$, 196 Si(NCO)$_4$

EXAMPLE 7

Preparation of Phenoxysilyl Triisocyanate in Toluene

To a slurry of sodium cyanate (39.0 gm, 0.6 mole) in sieve-dried toluene (100 ml) containing 18-crown-6 ether (0.8 gm, 3.03 m mole) as catalyst was slowly added phenoxytrichlorosilane (45.4 gm, 0.2 mole) over a period of 50 minutes. The temperature rose to 65° C. during the addition. The reaction mixture was then stirred at 61° C. for 1 hour and at 100° C. for an additional 5 hours. The sodium chloride was removed by filtration under a nitrogen atmosphere and was washed with 50 ml of toluene. Toluene was removed from the reaction mixture by distillation at atmospheric pressure and the phenoxysilyl triisocyanate was then distilled at 75°–80° C./5 mm Hg. The yield was 28.8 gms (58.4%)

IR: 2280, 2260 cm$^{-1}$ (NCO)

The oily residue (10 g) had an identical IR spectrum to the distillate.

EXAMPLE 8

Preparation of Phenylsilyl Triisocyanate in Toluene

To a slurry of sodium cyanate (75.0 gm, 1.15 mole) in sieve-dried toluene (150 ml) containing 18-crown-6 ether (1.2 gm, 4.54 m mole) as catalyst was slowly added phenyltrichlorosilane (60 ml, 0.375 mole). The temperature rose to 55° C. during the addition. The reaction mixture was then stirred at 70°–98° C. for 30 minutes and at 100°–110° C. for an additional 3½ hours, and was allowed to stand at 25° C. for 15 hours. Toluene was removed from the reaction mixture by distillation at atmospheric pressure and the phenylsilyl triisocyanate was then distilled at 132° C./15 mm Hg. The yield was 51.0 gms. (58.9%)

IR: 2270, 2300 cm$^{-1}$ (NCO)

EXAMPLE 9

Preparation of Silyl Triisocyanate in Dowtherm A

To a mixture of sodium cyanate (50.0 gm, 0.77 mole), 100 ml of Dowtherm A and 18-crown-6 ester (0.8 gm, 3.03 m mole) was added trichlorosilane (34.8 gm, 0.257 mole), over a period of ten minutes, with cooling. The reaction mixture was stirred at 25° C. for 1 hour and then at 58° C. for 3 hours. Unreacted trichlorosilane (7.1 gm) was distilled off at 30° C. and the silyl triisocyanate product was then distilled at 120° C.±5° C./115 mg Hg. The yield of product was 9.5 gm. (24.5%).

EXAMPLE 10

Preparation of Trimethylsilyl Isocyanate in Dowtherm A

Trimethylbromosilane (3.828 gm, 0.025 mole) was slowly added to a stirred mixture of sodium cyanate (1.625 gm, 0.025 mole), Dowtherm A (13 ml) and 18-crown-6 ether (32 mg), without any noticeable evolution of heat. The reaction mixture was then stirred at 65° C. for 3 hours and filtered to remove NaCl. Ha-100 NMR assay of the filtrate showed 77% unreacted trimethylbromosilane and 23% trimethylsilyl isocyanate product.

EXAMPLE 11

Preparation of Dimethylsilyl Diisocyanate in Heptane

A mixture of dimethyldichlorosilane (3.22 gm, 0.025 mole), sodium cyanate (3.25 gm, 0.05 mole), heptane (10 ml) and 18-crown-6 ether (60 mg) was stirred at 45° C. for 15 hours and then filtered to remove NaCl. HA-100 NMR assay of the reaction mixture filtrate indicated a 98% yield of dimethylsilyl diisocyanate in solution.

EXAMPLE 12

Preparation of Dimethylsilyl Diisocyanate in Methylene Chloride

The procedure of Example 11 was repeated except that the heptane used therein was replaced by an equal volume of methylene chloride. HA-100 NMR assay of the reaction mixture filtrate indicated a 95% yield of dimethylsilyl diisocyanate in solution.

EXAMPLE 13

Preparation of Dimethylsilyl Diisocyanate in 1,2-Dichloroethane (A) Dimethyldichlorosilane (3.22 gm, 0.025 mole) was slowly added to a mixture of sodium cyanate (3.25 gm, 0.05 mole), 1,2-dichloroethane (10 ml) and 18-crown-6 ether (60 mg), with no significant evolution of heat. The suspension was then stirred at 65° C. for 3½ hours and filtered to remove NaCl. HA-100 NMR assay of the reaction mixture filtrate indicated a 95% yield of dimethylsilyl diisocyanate in solution.

(B) The above reaction was repeated except that the crown ether was omitted and the reaction mixture was stirred at 50° C. for 24 hours. HA-100 NMR assay of the reaction mixture filtrate showed that no dimethylsilyl diisocyanate was produced.

EXAMPLE 14

Preparation of Dimethylsilyl Diisocyanate in Therminol 55

(A) The procedure of Example 13A was repeated except that the 1,2-dichloroethane used therein was replaced by an equal volume of Therminol 55 (dielectric constant=2-3). HA-100 NMR assay of the reaction mixture filtrate indicated a 95.8% yield of dimethylsilyl diisocyanate in solution.

(B) The above reaction was repeated except that the crown ether was omitted. HA-100 NMR assay of the reaction mixture filtrate showed that no dimethylsilyl diisocyanate was produced.

EXAMPLE 15

Preparation of Dimethylsilyl Diisocyanate in Ethyl Acetate

A mixture of sodium cyanate (1.3 gm, 0.02 mole), dimethyldichlorosilane (1.29 gm, 0.01 mole) and ethyl acetate (5 ml) was stirred with no apparent evolution of heat. There was then added 18-crown-6 ether (25 mg) and the temperature rose from 25° C. to 36° C. during one hour of stirring. The mixture was then stirred at 67° C. for an additional 17 hours and filtered to remove NaCl. HA-100 assay of the reaction mixture filtrate indicated an 87% yield of dimethylsilyl diisocyanate in solution.

IR: 2260, 2300 cm$^{-1}$ (NCO).

EXAMPLE 16

Preparation of Dimethylsilyl Diisocyanate in Methyl Benzoate (A) To a stirred suspension of sodium cyanate (3.25 gm, 0.05 mole) in 10 ml of methyl benzoate was slowly added dimethyldichlorosilane (3.22 gm, 0.025 mole). There was no apparent evolution of heat, so 18-crown-6 ether (60 mg) was added. This caused about 2° C. rise of temperature. The reaction mixture was stirrd at room temperature for B 2½ hours. NMR assay indicated only starting material so the reaction mixture was stirred at 60° C. for an additional hour and filtered to remove NaCl. HA-100 NMR assay of the reaction mixture filtrate then indicated a 98% yield of dimethylsilyl diisocyanate in solution.

(B) The above reaction was repeated except that the crown ether was omitted and the reaction mixture was stirred at 65° C. for 19 hours. HA-100 NMR assay of the reaction mixture filtrate showed that no dimethylsilyl diisocyanate was produced.

EXAMPLE 17

Preparation of Dimethylsilyl Diisocyanate in Silicone Oil (A) To a stirred suspension of sodium cyanate (3.25 gm, 0.05 mole), 10 ml of silicone oil (A. H. Thomas Co., Cat. No. 6428-R-15, dielectric constant=2.58) and 60 mg of 18-crown-6 ether was slowly added dimethyldichlorosilane (3.22 gm, 0.025 mole). A temperature rise of 24° C. was noted. The reaction mixture was then stirred at 65° C. for 4½ hours and filtered to remove NaCl. HA-100 NMR assay of the reaction mixture filtrate indicated a 100% yield of dimethylsilyl diisocyanate in solution.

(B) The above reaction was repeated except that the crown ether was omitted and the reaction mixture was stirred at 65° C. for 17 hours. HA-100 NMR assay showed that no dimethylsilyl diisocyanate was produced.

EXAMPLE 18

Preparation of Dimethylsilyl Diisocyanate in Mineral Oil (A) To a stirred suspension of sodium cyanate (3.25 gm, 0.05 mole), 10 ml of mineral oil (Extra Heavy, Purepac Co., dielectric constant=2.13) and 60 mg of 18-crown-6 ether was slowly added dimethyldichlorosilane (3.22 gm, 0.025 mole), and the mixture was stirred at 65° C. for 4½ hours and filtered to remove NaCl. HA-100 NMR assay of the reaction mixture filtrate indicated a 98% yield of dimethylsilyl diisocyanate in solution.

(B) The above reaction was repeated except that the crown ether was omitted and the reaction mixture was stirred at 65° C. for 17 hours. HA-100 NMR assay of the reaction mixture filtrate showed that no dimethylsilyl diisocyanate was produced.

EXAMPLE 19

Preparation of Dimethylsilyl Diisocyanate in Dowtherm A

To a stirred mixture of sodium cyanate (3.25 gm, 0.05 mole), 10 ml of Dowtherm A and 75 mg of 15-crown-5 ether was slowly added dimethyldichlorosilane (3.22 gm, 0.25 mole). A temperature rise of 11° C. was noted.

The mixture was stirred at 25° C. for 24 hours and filtered to remove NaCl. HA-100 NMR assay of the filtrate indicated a 90.8% yield of dimethylsilyl diisocyanate in solution.

EXAMPLE 20

Preparation of Ethylsilyl Triisocyanate in Dowtherm A

To a stirred slurry of sodium cyanate (50 gm, 0.77 mole), Dowtherm A (100 ml) and 18-crown-6 ether (0.8 gm) was slowly added ethyltrichlorosilane (40.8 gm, 0.25 mole) over a period of 1 hour. The reaction temperature rose from room temperature to 56° C. during the addition. The mixture was stirred at 55°-60° C. for an additional hour, at 110° C. for 1½ hours and then at room temperature for 3 days. Ethylsilyl triisocyanate was distilled directly from the reaction mixture. The first fraction (26.4 gms) distilled at 137°-140° C. at 143 mm Hg; a second fraction (19.0 gms) was distilled from the residual oil at 132°-146° C. at 116 mm Hg. Total yield of title product was 45.4 gms (99.1% of theory). Infrared analysis showed a strong sharp singlet NCO peak between 2270 and 2280 cm$^1$.

EXAMPLE 21

Preparation of Dimethylsilyl Diisocyanate in Dowtherm A

To a stirred slurry of sodium cyanate (32.5 gm, 0.5 mole), Dowtherm A (100 ml) and dibenzo-18-crown-6 ether (0.75 gm) was slowly added dimethyldichlorosilane (30.5 ml, 0.25 mole) over a period of 1½ hours, during which the temperature rose from 25° C. to 35° C. The reaction mixture was then stirred at 78° C. for 3½ hours, at 25° C. for 3½ days, at 80° C. for 30 minutes and at 130° C. for 30 minutes. Infrared analysis of the reaction mixture showed two NCO peaks at 2275 and 2310 cm$^{-1}$. Dimethylsilyl diisocyanate was distilled directly from the reaction mixture; b.p. 80°-85° C. under slightly reduced pressure. The yield of title product was 26.3 gms (72.0% of theory).

EXAMPLE 22

Preparation of Dimethylsilyl Diisocyanate in Dowtherm A

To a stirred slurry of sodium cyanate (3.25 gm, 0.05 mole), Dowtherm A (100 ml) and 12-crown-4 ether (0.075 gm) was added dimethyldichlorosilane (3.22 gm, 0.025 mole). No temperature rise was noted. The reaction mixture was stirred at 22° C. for 1½ hours, after which NMR analysis of the reaction mixture showed 97.4% starting dimethyldichlorosilane and 2.6% dimethylchlorosilyl isocyanate. The reaction mixture was then stirred at 70° C. for 2 hours and 90° C. for 1 hour, after which NMR analysis of the mixture showed 86.5% of the desired dimethylsilyl diisocyanate along with 11% of dimethylchlorosilyl isocyanate and 1.5% of dimethyldichlorosilane.

EXAMPLE 23

Preparation of Dimethylsilyl Diisocyanate in Dowtherm A

The general procedure of Example 2A is repeated except that the 18-crown-6 ether utilized therein is replaced by an equivalent amount of
benzo-15-crown-5 ether,
4-tert-butylbenzo-15-crown-5 ether,
4-tert-butylcyclohexo-15-crown-5 ether,
21-crown-7 ether,
cyclohexo-15-crown-5 ether,
1,10-diaza-18-crown-6 ether,
dicyclohexo-18-crown-6 ether,
2,6-diketo-18-crown-6 ether,
1,10-dithia-18-crown-6 ether and
1,4,7-trithia-15-crown-5 ether, respectively, and dimethylsilyl diisocyanate is produced in each instance.

EXAMPLE 24

Preparation of Dimethylsilyl Diisocyanate in Dowtherm A

The general procedure of Example 2A is repeated except that the sodium cyanate utilized therein is replaced by an equivalent amount of lithium cyanate and potassium cyanate, respectively, and dimethylsilyl diisocyanate is produced in each instance.

EXAMPLE 25

The general procedure of Example 5 is repeated except that the methyltrichlorosilane utilized therein is replaced by an equimolar amount of
methoxytrichlorosilane,
ethoxytrichlorosilane,
benzyltrichlorosilane,
benzyloxytrichlorosilane and
n-propyltrichlorosilane, respectively,
and there is thereby produced
methoxysilyl triisocyanate,
ethoxysilyl triisocyanate,
benzylsilyl triisocyanate,
benzyloxysilyl triisocyanate and
n-propylsilyl triisocyanate, respectively.

We claim:

1. A process for the preparation of a silyl isocyanate of the formula

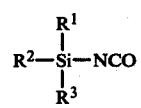
I wherein R$^1$, R$^2$ and R$^3$ each are independently hydrogen, isocyanato, (lower)alkyl, (lower)alkoxy, phenyl, phenoxy, phenyl(lower)alkyl, phenyl(lower)alkoxy or cycloalkyl; which process comprises reacting a halogen compound of the formula

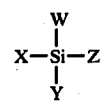
II wherein W is R$^1$, chloro, bromo, fluoro or iodo; X is R$^2$, chloro, bromo, fluoro, or iodo; Y is R$^3$, chloro, bromo, fluoro or iodo; and Z is chloro, bromo, fluoro or iodo; with from about 1 to about 1.5 equivalents of an alkali metal cyanate for each halogen present in compound II, in an inert solvent having a dielectric constant below about 10, at a temperature of from about 0° C. to about 200° C., in the presence of a crown ether as a catalyst.

2. The process of claim 1 for the preparation of a silyl isocyanate of the formula

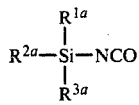

wherein $R^{1a}$, $R^{2a}$ and $R^{3a}$ each are independently hyrogen, isocyanato, (lower)alkyl, (lower)alkoxy, phenyl or phenoxy; which comprises reacting a halogen compound of the formula

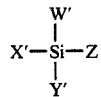

wherein W' is $R^{1a}$, chloro, bromo, fluoro or iodo; X' is $R^{2a}$, chloro, bromo, fluoro, iodo; Y' is $R^{3a}$, chloro, bromo, fluoro or iodo; and Z is chloro, bromo, fluoro or iodo; with from about 1 to about 1.5 equivalents of sodium cyanate or potassium cyanate for each halogen present in compound II', in an inert solvent having a dielectric constant below about 10, at a temperature of from about 25° C. to about 150° C., in the presence of a crown ether as a catalyst.

3. The process of claim 2 in which the crown ether catalyst is 18-crown-6 ether, dibenzo-18-crown-6 ether, 1,10-diaza-18-crown-6 ether, dicyclohexo-18-crown-6 ether, 2,6-diketo-18-crown6 ether, 1,10-dithia-18-crown6 ether, 15-crown-5 ether, benzo-15-crown-5 ether, 4-tert-butylbenzo-15-crown-5 ether, 4-tert-butylcyclohexo-15-crown-5 ether, cyclohexo-15-crown-5 ether, 1,4,7-trithia-15-crown-5 ether, 21-crown-7 ether or 12-crown-4 ether.

4. The process of claim 3 for the preparation of a silyl isocyanate of the formula

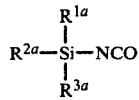

wherein $R^{1a}$, $R^{2a}$ and $R^{3a}$ each are independently hydrogen, isocyanato or (lower)alkyl; which process comprises reacting a halogen compound of the formula

wherein W' is $R^{1a}$, chloro, bromo or fluoro; X' is $R^{2a}$, chloro, bromo or fluoro; Y' is $R^{3a}$, chloro, bromo or fluoro; and Z is chloro, bromo or fluoro; with from about 1 to about 1.5 equivalents of sodium cyanate for each halogen present in compound II'; in an inert solvent having a dielectric constant below about 10, at a temperature of from about 25° C. to about 150° C.

5. The process of claim 2 in which the crown ether catalyst is 18-crown-6 ether, dibenzo-18-crown-6 ether, 15-crown-5 ether or 12-crown-4 ether.

6. The process of claim 4 in which the crown ether catalyst is 18-crown-6 ether, dibenzo-18-crown-6 ether, 15-crown-5 ether or 12-crown-4 ether.

7. The process of claim 2 in which the crown ether catalyst is 18-crown-6 ether.

8. The process of claim 4 in which the crown ether catalyst is 18-crown-6 ether.

9. A process for the preparation of a silyl isocyanate of the formula $$[(lower)alkyl]_n Si(NCO)_{4-n}$$

wherein n is an integer of from 1 to 4, inclusive, which process comprises reacting a silyl halide of the formula $$[(lower)alkyl]_n Si(Hal)_{4-n}$$

wherein n is as defined above and Hal is chloro, bromo, fluoro or iodo, with an n equivalent parts of sodium cyanate in an inert solvent having a dielectric constant below about 10, at a temperature of from about 25° C. to about 150° C., in the presence of from about 0.1% to about 10% by weight of 18-crown-6 ether based on the weight of silyl halide.

10. The process of claim 9 wherein the inert solvent is a mixture of biphenyl and diphenyl ether.

* * * * *

UNITED STATES PATENT AND TRADEMARK OFFICE
CERTIFICATE OF CORRECTION

PATENT NO. : 4,176,131
DATED : November 27, 1979
INVENTOR(S) : Kun M. Shih and Derek Walker It is certified that error appears in the above-identified patent and that said Letters Patent are hereby corrected as shown below:

In Column 2, Line 7: "$R_n Si(NOC)_{4-n}$" should read --$R_n Si(NCO)_{4-n}$--.

In Claim 2 (Column 13, Lines 8 and 9): "hyrogen" should read --hydrogen--.

In Claim 2 (Column 13, Line 31): "2,6-diketo-18-crown6 ether" should read --2,6-diketo-18-crown-6 ether--.

In Claim 3 (Column 13, Line 32): "crown6 ether" should read --crown-6 ether--.

In Claim 9 (Column 14, Line 37): "with an n equivalent" should read --with about n equivalent--.

Signed and Sealed this

Eighteenth Day of March 1980

[SEAL]

Attest:

SIDNEY A. DIAMOND

Attesting Officer

Commissioner of Patents and Trademarks